United States Patent
Egyed et al.

(10) Patent No.: US 7,148,191 B2
(45) Date of Patent: Dec. 12, 2006

(54) ANTIGENIC COMPOSITION

(75) Inventors: Alena Egyed, Vienna (AT); Karen Lingnau, Vienna (AT); Frank Mattner, Vienna (AT); Michael Buschle, Perchtoldsdorf (AT); Walter Schmidt, Vienna (AT)

(73) Assignee: Intercell AG, Vienna (AT)

( * ) Notice: Subject to any disclaimer, the term of this patent is extended or adjusted under 35 U.S.C. 154(b) by 444 days.

(21) Appl. No.: 10/297,497

(22) PCT Filed: Jun. 7, 2001

(86) PCT No.: PCT/EP01/06437

§ 371 (c)(1),
(2), (4) Date: Dec. 6, 2002

(87) PCT Pub. No.: WO01/93903

PCT Pub. Date: Dec. 13, 2001

(65) Prior Publication Data

US 2003/0162738 A1    Aug. 28, 2003

(30) Foreign Application Priority Data

Jun. 8, 2000  (AT) ............................ A 1000/2000

(51) Int. Cl.
*A61K 38/00* (2006.01)
*A61K 31/70* (2006.01)
(52) U.S. Cl. ............................ 514/2; 514/12; 514/44
(58) Field of Classification Search .................... None
See application file for complete search history.

(56) References Cited

U.S. PATENT DOCUMENTS

| 3,679,654 A | 7/1972 | Maes | 260/112.5 |
| 3,725,545 A | 4/1973 | Maes | 424/180 |
| 6,008,334 A | 12/1999 | Hanna | 536/22.1 |
| 2003/0095979 A1* | 5/2003 | Mattner et al. | 424/185.1 |

FOREIGN PATENT DOCUMENTS

WO   WO 97/30721   8/1997

OTHER PUBLICATIONS

Harrington et al. 1979, Infection and Immunity, vol. 24, pp. 160-166.*
Bloom et al., "Identification of tyrosinase-related protein 2 as a tumor rejection antigen for the B16 melanoma," *J. of Experimental Medicine*, 185(3):453-459, 1997.
Buschle et al., "Chemically defined, cell-free cancer vaccines: use of tumor antigen-derived peptides or polyepitope proteins for vaccination," *Gene Therapy and Molecular Biology*, 1:309-321, 1998.
Buschle et al., "Transloading of tumor antigen-derived peptides into antigen-presenting cells," *Proc. Natl. Acad. Sci., USA*, 94:3256-3261, 1997.
Cavanaugh et al., "The activation of murine macrophages and natural killer cells by the partially thiolated double stranded RNA poly (I)-mercapto poly (C)," *Research Communications in Molecular Pathology and Pharmacology*, 91(2):131-147, 1996.
Cella et al., "Maturation, activation, and protection of dendritic cells induced by double-stranded RNA," *J. Exp. Med.*, 189(5):821-829, 1999.
Guggenheim and Baron, "Clinical studies of an interferon inducer, polyriboinosinic-polyribocytidylic acid [Poly (I) Poly (C)], in children," *Journal of Infectious Disease*, 136:50-58, 1977.
Harrington et al., "Adjuvant effects of low doses of a nuclease-resistant derivative of polyniosinic acid polyctydiylic acid on antibody responses of monkeys to inactivated Venezuelan equine encephalomyelitis virus vaccine," *Infection and Immunity*, 24:160-166, 1979.
Hoffman et al., "Phylogenetic perspective in innate immunity," *Science*, 284:1313-1317, 1999.
Lethe et al., "Mouse tumor rejection antigens P815A and P815B: two epitopes carried by a single peptide," *Eur. J. Immunol.*, 22:2283-2288, 1992.
Manetti et al., "Polyinosinic acid: polycytidylic acid promotes T helper type 1-specific immune response by stimulating macrophage production of interferon-α and interleukin-12," *Eur J. Immunol.*, 25:2656-2660, 1995.
Salazar et al., "Long-term treatment of malignant gliomas with intramuscularly administered polyinosinic-polycytidylic acid stabilized with polylysine and carboxymethylcellulose: an open pilot study," *Neurosurgery*, 38:1096-1104, 1996.
Schmidt et al., "Cell-free tumor antigen peptide-based cancer vaccines," *Proc. Natl. Acad. Sci., USA*, 94:3262-3267, 1997.
Simmler et al., "Clinical trial of Poly I-Poly C as an immunity adjuvant and an immunorestoration agent," *Europ. J. Cancer*, 13:463-467, 1997.
Singh and O'Hagan, "Advances in vaccine adjuvants," *Nat. Biotechnology*, 17:1075-1081, 1999.
Verdijk et al., "Polyriboinosinic polyribocytidylic acid (Poly(I:C)) incuces stable maturation of functionally active human dendritic cells," *J. of Immunology*, 163:57-61, 1999.

* cited by examiner

*Primary Examiner*—B. Dell Chism
(74) *Attorney, Agent, or Firm*—Fulbright & Jaworski

(57) ABSTRACT

The invention relates to a composition comprising
  a T cell epitope or a mixture of T cell epitopes
  a polycationic peptide and
  a nucleic acid based on inosin and cytosin and its use as a vaccine.

22 Claims, 9 Drawing Sheets

A)

B)

SEQUENCE LISTING

<160> NUMBER OF SEQ ID NOS: 4

<210> SEQ ID NO 1

```
<211> LENGTH: 8
<212> TYPE: PRT
<213> ORGANISM: Artificial
<220> FEATURE:
<223> OTHER INFORMATION: Synthetic Peptide

<400> SEQUENCE: 1

Val Tyr Asp Phe Phe Val Trp Leu
1               5

<210> SEQ ID NO 2
<211> LENGTH: 9
<212> TYPE: PRT
<213> ORGANISM: Artificial
<220> FEATURE:
<223> OTHER INFORMATION: Synthetic Peptide

<400> SEQUENCE: 2

Leu Pro Tyr Leu Gly Trp Leu Val Phe
1               5

<210> SEQ ID NO 3
<211> LENGTH: 8
<212> TYPE: PRT
<213> ORGANISM: Artificial
<220> FEATURE:
<223> OTHER INFORMATION: Synthethic Peptide

<400> SEQUENCE: 3

Ser Ile Ile Asn Phe Glu Lys Leu
1               5

<210> SEQ ID NO 4
<211> LENGTH: 16
<212> TYPE: PRT
<213> ORGANISM: Artificial
<220> FEATURE:
<223> OTHER INFORMATION: Synthetic Peptide

<400> SEQUENCE: 4

Thr Glu Trp Thr Ser Ser Asn Val Met Glu Glu Arg Lys Ile Lys Val
1               5                   10                  15
```

ANTIGENIC COMPOSITION

This application is a U.S. national phase application under 35 U.S.C. § 371 of PCT Application No. PCT/EP01/06437 filed 7 Jun. 2001, which claims priority to Austrian Application No. A 1000/2000 filed 8 Jun. 2000.

BACKGROUND OF THE INVENTION

A vaccine can contain a whole variety of different antigens. Examples of antigens are whole-killed organisms such as inactivated viruses or bacteria, fungi, protozoa or even cancer cells. Antigens may also consist of subfractions of these organisms/tissues, of proteins, or, in their most simple form, of peptides. Antigens can also be recognized by the immune system in form of glycosylated proteins or peptides and may also be or contain polysaccharides or lipids. Short peptides can be used since for example cytotoxic T cells (CTL) recognize antigens in form of short usually 8–11 amino acids long peptides in conjunction with major histocompatibility complex (MHC) (Rammensee et al., 1995).

In order to obtain sustained, antigen-specific immune responses, adjuvants need to trigger immune cascades that involve all cells of the immune system necessary. Primarily, adjuvants are acting, but are not restricted in their mode of action, on so-called antigen presenting cells (APC), of which dendritic cells (DCs) are the most potent. These cells usually first encounter the antigen(s) followed by presentation of processed or unmodified antigen to immune effector cells. Intermediate cell types may also be involved. Only effector cells with the appropriate specificity are activated in a productive immune response. The adjuvants may also locally retain antigens and co-injected other factors. In addition, the adjuvants may act as a chemoattractant for other immune cells or may act locally and/or systemically as a stimulating agent for the immune system.

Cells of the innate immune system recognize patterns expressed on their respective targets. Examples are lipopolysaccharides (LPS) in the case of Gram-negative bacteria, mycobacterial glycolipids, lipoteichoic acids of Gram-positive bacteria, mannans of yeast and double stranded RNAs of viruses (Hoffmann et al., 1999). In addition, they may recognize patterns such as altered glycosylations of proteins on tumor cells.

Polycationic polymers, for example the polycationic amino acid polymers poly-L-arginine and poly-L-lysine, have been shown to allow very efficient charging of APC with antigens in vitro and in vivo (Buschle et al., 1998, Buschle et al., 1997, Schmidt et al., 1997). This is thought to be the key event for triggering immune cascades, eventually leading to the induction of antigen-specific immune effector cells that are able to destroy or neutralize targets. It has been shown previously that a number of polycationic compounds exert effects on immune cells (Buschle et al., 1998, Buschle et al., 1997).

Co-injection of a mixture of poly-L-arginine or poly-L-lysine together with an appropriate antigen as a vaccine protects animals from tumor growth in several animal models (Buschle et al., 1998, Schmidt et al., 1997). This chemically defined vaccine is able to induce a high number of antigen-specific T cells. In order to induce antigen-specific T cells, peptides need to be taken up by APC. Such peptide-loaded APC will induce an immune cascade, eventually leading to the induction of antigen-specific immune effector cells like T cells.

Polyinosinic-polycytidylic acid (poly I:C) is known as a potent interferon type I inducer (Manetti et al., 1995). Because of its protective effects in a number of animal species against a broad spectrum of both RNA and DNA viruses (e.g., herpes simplex virus, rabies virus, Japanese B encephalitis virus, vaccinia virus, encephalomyocarditis virus), poly I:C is often used in models of viral infections. Changes that occur in response to poly I:C are thought to be representative of changes that occur in response to a variety of different viruses. Poly I:C is known to stimulate macrophages to produce cytokines such as IL-la and IL-12 (Manetti et al., 1995), it is a potent NK cell stimulator (Cavanaugh et al., 1996) and, in general, this compound is known to promote Th1-specific immune responses. Because of these abilities, poly I:C has been widely applied as an immunomodulator in several clinical trials showing little or no toxicity (Guggenheim et al., 1977, Simnaler et al., 1977). However, there was no patient benefit. It is unclear whether poly I:C on its own has adjuvant activity. Recent findings show that poly I:C also induces stable maturation of in vitro-cultured DCs and that such DCs are potent T cell stimulators in vitro (Cella et al., 1999; Verdijk et al., 1999).

SUMMARY OF THE INVENTION

It is an object of the present invention to provide an effective vaccine system to allow an effective delivery of a specific antigen to the immune system of man or animal to achieve an efficient immunization against such an antigen.

This object is solved by a pharmaceutical composition comprising a T cell epitope (i.e. an antigen recognized by T cells) or mixtures of T cell epitopes, a polycationic peptide and a nucleic acid based on inosine and cytosine.

It has surprisingly turned out that, although polycationic peptides and nucleic acids based on inosine and cytosine have been previously known as being efficient adjuvant substances, the combination of both substances with a T cell epitope shows synergistic effects in immunostimulation which by far exceeds their additive contributions.

Moreover, whereas in previous uses of polycationic peptides and/or nucleic acids based on inosine and cytosine in vaccines only large antigens or whole cell vaccines have been used (where no synergistic effect of the two components may be seen), it could be shown by the present invention that on a T cell level antigens may be provided in a vaccine which gives an efficient T cell response. Immunisation with large antigens or even whole cells, results in the generation of antibodies. According to the present invention, such antibody generation is not an object. Therefore, the compositions according to the present invention preferably contain antigens lacking B-cell epitopes and containing only antigens having one or more specific T cell epitope(s).

Indeed, it could be shown that also weakly immunogenic T cell epitopes which normally give no T cell response ("normally"=either alone, with adjuvants according to the prior art or with only one immunostimulatory substance according to the present invention), may be formulated into very efficient T cell vaccines by combining it with a polycationic polypeptide and a nucleic acid based on inosine or cytosine. Therefore, vaccines according to the present invention may also comprise T cell epitopes which do not result in a sufficient T cell response under "normal" conditions (i.e. in vaccine compositions according to the prior art as defined above). The term "antigen" hereinafter relates to "T cell epitope(s)".

Especially antigens may be successfully used in the present invention, which do not result in a sufficient immune response when applied with alumn, the standard adjuvant (or other prior art adjuvants are disclosed e.g. in Singh et al.

(Nat. Biotechnol. 17 (1999), 1075–1081)) or with polycationic polypeptides or nucleic acids based on inosine and cytosine alone. A sufficient immune response may be regarded e.g. resulting in more than 50, preferably more than 200, especially more than 400 IFN-γ spots/$10^6$ unseparated cells in an Elispot-assay.

Preferably, the nucleic acid based on inosine and cytosine is selected from poly I: poly C, poly IC, poly dC: poly dI and poly dIC. Of course, any other combinations of complementary double-stranded IC sequences are also preferred as well as chemically modified nucleic acids, e.g. thiolated poly IC as described in U.S. Pat. Nos. 6,008,334; 3,679,654 and 3,725,545.

Polycationic peptides to be used in the present invention are e.g. described in the WO97/30721. Preferred polycationic peptides are poly-lysines, poly-arginines and polypeptides containing more than 50% of basic amino acids, especially arginine or lysine residues, in a range of more than 5, especially more than 8 amino acid residues or mixtures thereof. These polycationic peptides may be produced chemically or recombinantly or may be derived from natural sources. Preferred polycationic peptides derived from natural sources include HIV-rev or HI-tat derived cationic peptides, antennapedia peptides, cationic antimicrobial peptides, defensins, chitosan (or other derivates of chitin) and other peptides derived from these peptides or proteins by a biochemial recombinant production. Preferably, the polycationic peptides contain between 10 and 1000 residues, especially between 50 and 500 residues. Preferably, these peptides contain more than 70%, especially more than 85% basic amino acid residues, such as arginine, lysine, ornithine etc., and also synthetic organic polycations-(polypeptide-like substances), like polyethyleneimine, histones, protamine, as disclosed in the WO97/30721. Of course, also mixtures of different polycationic peptides or polypeptides may be used.

The antigens to be used in the present composition are not critical. Preferably, peptides derived from a viral or a bacterial pathogen or from fungi or parasites are used as such antigens (including derivatized antigens or glycosylated or lipidated antigens or polysaccharides or lipids). Preferred (human, animal and plant) pathogens are selected from HIV, HBV, HCV, Influenza virus, *Rotavirus*, *Staphylococcus aureus*, *Chlamydia pneumoniae*, *Mycobacterium tuberculosis*, *Streptococcus pneumoniae*, *Bacillus anthracis*, *Vibrio cholerae*, *Plasmodium* sp. (*Pl. falciparum*, *Pl. vivax*, etc.), *Aspergillus* sp. or *Candida albicans*. The derivation process may include the purification of a specific protein from the pathogen, the inactivation of the pathogen as well as the proteolytic or chemical derivatization or stabilization of such a protein. Alternatively, also parts of the pathogen itself may be used as an antigen. In the same way also tumor antigens (cancer vaccines) or autoimmune antigens may be used in the pharmaceutical composition according to the present invention. With such compositions a tumor vaccination or a treatment for autoimmune diseases may be performed.

The antigens are preferably peptide or protein, carbohydrate or lipid antigens or mixtures thereof. Antigens from parasites or plant pathogens are also preferred.

Preferably, the antigen is a peptide consisting of 6 to 20, preferably, 7 to 15, especially 8 to 11, amino acid residues. Antigens of this length have been proven to be especially suitable for T cell activation.

According to another aspect the present invention relates also to the use of a composition according to the present invention for the preparation of a vaccine.

The relative amounts of the ingredients of the present composition are highly dependent on the necessities of the individual composition, e.g. the polycationic peptide to be used. Preferably between 1 μg and 1 g of antigen, polycationic peptide and nucleic acid based on inosin and cytosin are applied. In case of poly-L-arginine and poly-L-lysine, preferred amounts of antigen/polypeptide/nucleic acid based on inosine and cytosine lie in the range of 1–10000 μg antigen per vaccination and 0.1 to 1000 μg polypeptid. The amount of poly IC may preferably range from 1 to 5000 μg/kg body weight (10 μg–500 mg).

The composition according to the present invention may further contain auxiliary substances, such as buffers, salts, stabilizers, antioxidants, etc., or other effective substances, such as antiinflammatoric or antinociceptive drugs.

The present compositions may be applied to a patient, e.g. a vaccination candidate, in efficient amounts, e.g. by weekly, biweekly or monthly intervals. Patients to be treated with the present composition may also be vaccinated repeatedly or only once. A preferred use of the present invention is the active immunization, especially of humans or animals without protection against the specific antigen.

The route of application for the present composition is not critical, e.g. subcutaneous, intramuscular, intradermal or transdermal injection is suitable as well as oral uptake. It is also possible to apply the present composition separately, e.g. by injecting the nucleic acid based on inosine and cytosine separately from the antigen/polycationic peptide composition. The present invention is therefore also directed to a kit comprising a composition containing the antigen and the polycationic peptide as one component and a composition containing the nucleic acid based on inosine and cytosine as a second component. The components may be applied at the same time or site, however, an application at different sites or at a different time or for a different time period is also possible. It is also possible to vary the systemic or local applications of the composition or the components, respectively.

The present invention further relates to the use of the compositions according to the present application for the preparation of a vaccine inducing a systemic immune response.

BRIEF DESCRIPTION OF THE DRAWINGS

Details of the present invention are described by the following examples and the figures, but the invention is of course not limited thereto.

DETAILED DESCRIPTION OF THE INVENTION

EXAMPLES

Example 1

The combined injection of polyinosinic-polycytidylic acid (pIC) and poly-L-arginine (pR) synergistically enhances the immune response against ovalbumin-derived peptide.

| | |
|---|---|
| Mice | C57B1/6 (Harlan/Olac) |
| Peptide | OVA$_{257-264}$-Peptide (SIINFEKL), an MHC class I (H-2K$^b$)-restricted epitope of chicken ovalbumin (Rotzschke et al., 1991), was synthesized using standard solid phase F-moc synthesis, HPLC purified and analyzed by mass spectroscopy for purity. Dose: 300 μg/mouse |

-continued

| | |
|---|---|
| Poly-L-Arginine (pR) | Poly-L-Arginine with an average degree of polymerization of 60 arginine residues; SIGMA Chemicals Dose: 100 µg/mouse |
| Polyinosinic-polycytidylic acid (pIC) | polyinosinic-polycytidylic acid (Sigma Chemicals, P-0913, Lot 125H4024) with the molecular weight between 220,000 to 460,000 Dose: 100 µg/mouse |

Figure 1:
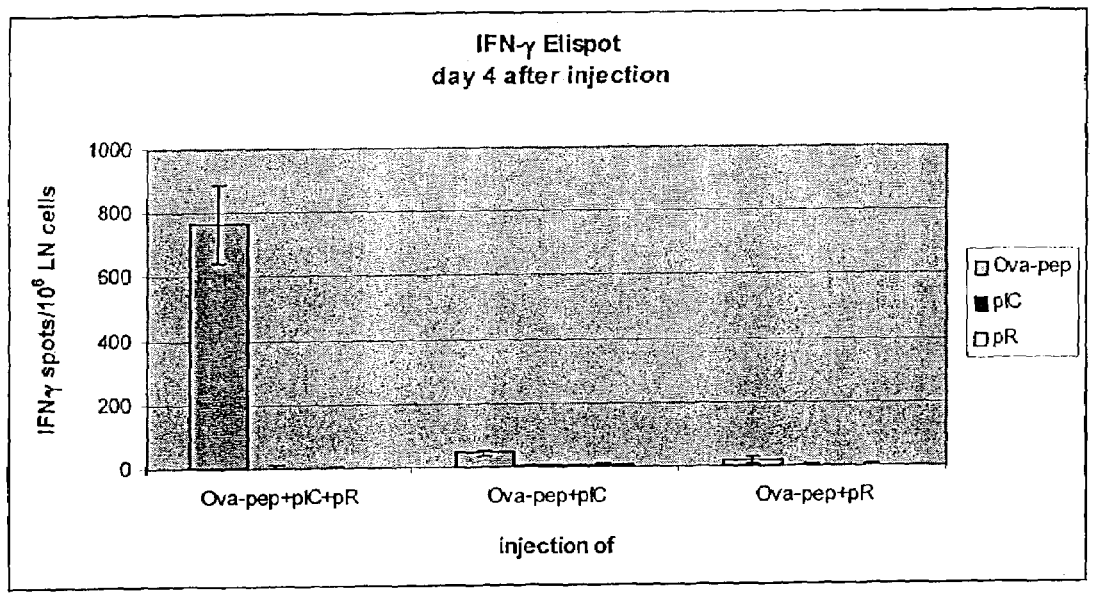
FIG. 1 shows the immune response against ovalbumin-derived peptide of a combined injection of polyinosinic-polycytidylic acid (pIC) and poly-L-arginine (pR); Mice were injected subcutaneously into the footpad with mixtures as indicated. Four days later, draining lymph nodes (LN) were taken and lymph node cells were re-stimulated either with ova-derived peptide, pIC or pR. Number of IFN-γ-producing cells was determined 24 hours later using an ELISPOT assay. Results are expressed as the number of spots/$1 \times 10^6$ LN cells±SD of triplicates.

Experimental Groups (4 Mice Per Group)
1. $OVA_{257-264}$-peptide+pIC+pR
2. $OVA_{257-264}$-peptide+pIC
3. $OVA_{257-264}$-peptide+pR On day 0 mice were injected into each hind footpad with a total volume of 100 µl (50 µl per footpad) containing the above mentioned compounds. Animals were sacrificed 4 days after injection and popliteal lymph nodes were harvested. Single cell suspensions were prepared by mincing lymph nodes through a 70 µm cell strainer. Thereafter, cells were washed twice with DMEM medium (Life Technologies) containing 5% fetal calf serum (FCS, SIGMA Chemicals). Cells were adjusted to $10^7$ cells/ml in DMEM/5% FCS. IFN-γ ELISPOT assays were carried out in triplicates as described (Miyahira et al., 1995). This method is a widely used procedure for the quantification of antigen-specific T cells. Lymph node cells were re-stimulated in vitro either with Ova-peptide, polyinosinic-polycytidylic acid (pIC), poly-L-arginine (pR), Concanavalin A (ConA) or medium alone (background). Each spot represents a single IFN-γ-producing T cell. Spots were counted using a Biosys reader (Biosys, Germany). Number of background spots was subtracted from all samples. The Results are expressed as the number of spots/$1 \times 10^6$ unseparated cells±SD of triplicates. After the stimulation with ConA we could detect many spots (data not shown) indicating a good condition of the used lymphocytes. As shown in FIG. 1, by injecting Ova-derived peptide with a combination of pIC and pR, we could induce almost 800 peptide-specific T cells among one million lymph node cells. In contrast, injections of peptide with either of the substances alone failed to induce peptide-specific T cells (FIG. 1).

Example 2

The combined injection of pIC and pR enhances the immune response against ovalbumin-derived peptide in a concentration (pIC)-dependent manner.

| | |
|---|---|
| Mice | C57B1/6 (Harlan/Olac) |
| Peptide | $OVA_{257-264}$-Peptide (SIINFEKL), an MHC class I ($H-2K^b$)-restricted epitope of chicken ovalbumin (Rotzschke et al., 1991), was synthesized using standard solid phase F-moc synthesis, HPLC purified and analyzed by mass spectroscopy for purity. Dose: 300 µg/mouse |
| Poly-L-Arginine (pR) | Poly-L-Arginine with an average degree of polymerization of 60 arginine residues; SIGMA Chemicals Dose: 100 µg/mouse |
| Polyinosinic-polycytidylic acid (pIC) | polyinosinic-polycytidylic acid (Sigma Chemicals, P-0913, Lot 125H4024) with the molecular weight ranging from 220,000 to 460,000 Dose: 100, 50, 25 µg/mouse |

Figure 2:
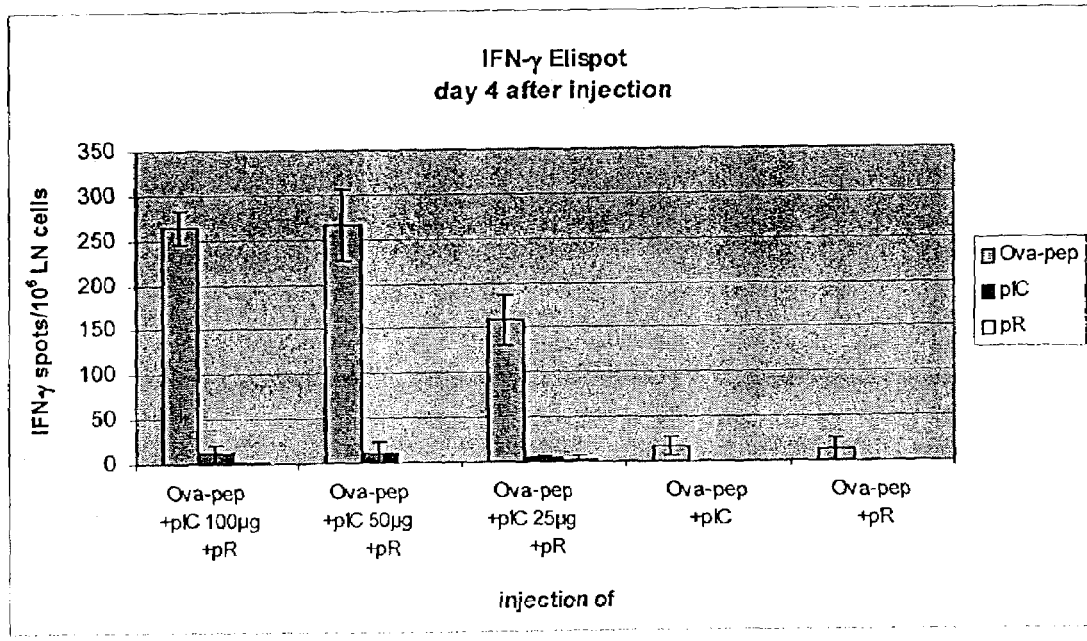
FIG. 2 shows the immune response against ovalbumin-derived peptide of a combined injection of pIC and pR; Mice were injected subcutaneously into the footpad with mixtures as indicated. Four days later, draining lymph nodes (LN) were taken and lymph node cells were re-stimulated either with Ova-derived peptide, pIC or pR. Number of IFN-γ-producing cells was determined 24 hours later using an ELISPOT assay. Results are shown as the number of spots/$1 \times 10^6$ LN cells±SD of triplicates.

Experimental Groups (4 Mice Per Group)
1. $OVA_{257-264}$-peptide+pIC 100 µg+pR
2. $OVA_{257-264}$-peptide+pIC 50 µg+pR
3. $OVA_{257-264}$-peptide+pIC 25 µg+pR
4. $OVA_{257-264}$-peptide+pIC 100 µg
5. $OVA_{257-264}$-peptide+pR On day 0 mice were injected into each hind footpad with a total volume of 100 µl (50 µl per footpad) containing the above mentioned compounds. Animals were sacrificed 4 days after injection and popliteal lymph nodes were harvested. Lymph node cell suspensions were prepared and IFN-γ ELISPOTs were performed as described in example 1. Results are expressed as the number of spots/$1 \times 10^6$ cells±SD of triplicates. Even very low dose of pIC (25 µg/mouse) injected in a combination with pR plus peptide leads to the induction of antigen-specific T cells (FIG. 2).

Example 3

The combined injection of pIC and pR enhances the induction of ovalbumin-peptide-specific T cells in a peptide concentration-dependent manner.

| | |
|---|---|
| Mice | C57B1/6 (Harlan/Olac) |
| Peptide | $OVA_{257-264}$-Peptide (SIINFEKL), an MHC class I ($H-2K^b$)-restricted epitope of chicken ovalbumin (Rotzschke et al., 1991), was synthesized using standard solid phase F-moc synthesis, HPLC purified and analysed by mass spectroscopy for purity. Dose: 300, 100, 50 µg/mouse |
| Poly-L-Arginine (pR) | Poly-L-Arginine with an average degree of polymerization of 60 arginine residues; SIGMA Chemicals Dose: 100 µg/mouse |
| Polyinosinic-polycytidylic acid (pIC) | polyinosinic-polycytidylic acid (Sigma Chemicals, P-0913, Lot 125H4024) with the molecular weight ranging from 220,000 to 460,000 Dose: 100 µg/mouse |

Figure 3:
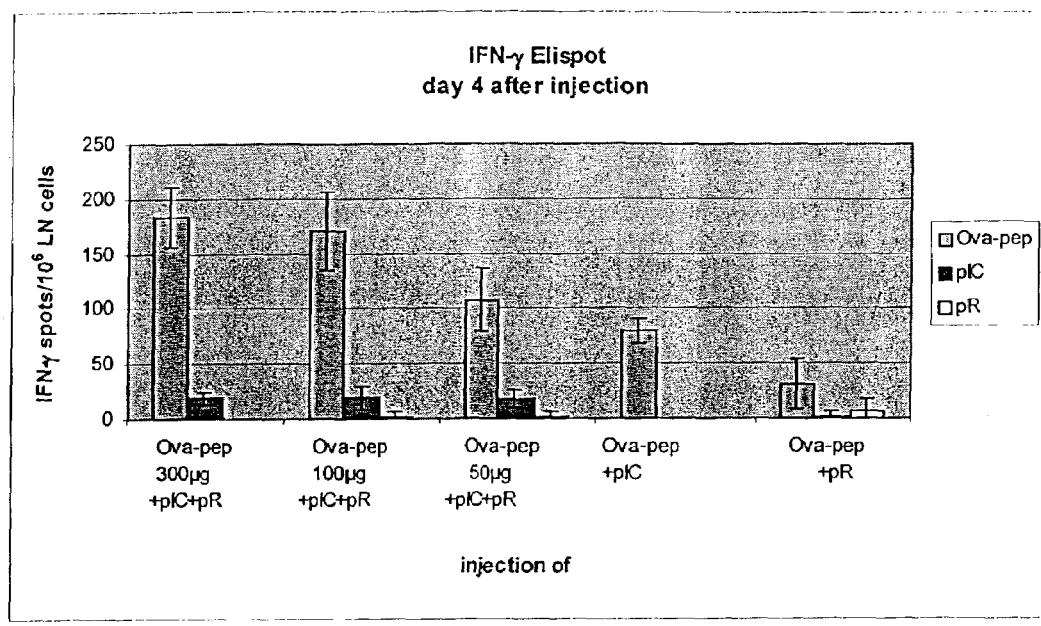
FIG. 3 shows the induction of ovalbumin-peptide specific T cells after combined injection of pIC and pR; Mice were injected subcutaneously into the footpad with mixtures as indicated. Four days later, draining lymph nodes (LN) were taken and lymph node cells were re-stimulated either with Ova-derived peptide, pIC or pR. Number of IFN-γ-producing cells was determined 24 hours later using an ELISPOT assay. Results are shown as the number of spots/1×10$^6$ LN cells±SD of triplicates.

Experimental Groups (4 Mice Per Group)
1. $OVA_{257-264}$-peptide 300 µg+pIC+pR
2. $OVA_{257-264}$-peptide 100 µg+pIC+pR
3. $OVA_{257-264}$-peptide 50 µg+pIC+pR
4. $OVA_{257-264}$-peptide 300 µg+pIC
5. $OVA_{257-264}$-peptide 300 µg+pR On day 0 mice were injected into each hind footpad with a total volume of 100 µl (50 µl per footpad) containing the above mentioned compounds. Animals were sacrificed 4 days after injection and popliteal lymph nodes were harvested. Lymph node cell suspensions were prepared and IFN-γ ELISPOTs were performed as described in example 1. Results are expressed as the number of spots/$1 \times 10^6$ cells±SD of triplicates. As shown in FIG. 3, comparably strong immune response can be induced even when lower peptide dose (100 μg instead of 300 μg/mouse) is used for the vaccination.

Example 4

The combined injection of pIC and pR synergistically enhances the immune response against a TRP-2 (mouse tyrosinase-related protein-2)-derived peptide.

| Mice | C57B1/6 (Harlan/Olac) |
|---|---|
| Peptide | TRP-2-Peptide (VYDFFVWL), an MHC class I (H-2K$^b$)-restricted epitope of mouse tyrosinase-related protein-2 (Bloom et al., 1997) was synthesized by standard solid phase F-moc synthesis, HPLC purified and analysed by mass spectroscopy for purity. Dose: 100 μg/mouse |
| Poly-L-arginine (pR) | Poly-L-arginine with an average degree of polymerization of 60 arginine residues; SIGMA Chemicals Dose: 100 μg/mouse |
| Polyinosinic-polycytidylic acid (pIC) | polyinosinic-polycytidylic acid (Sigma Chemicals, P-0913, Lot 125H4024) with the molecular weight ranging from 220,000 to 460,000 Dose: 100 μg/mouse |

Experimental Groups (4 Mice Per Group)
1. TRP-2+pIC+pR
2. TRP-2+pIC
3. TRP-2+pR

Figure 4:
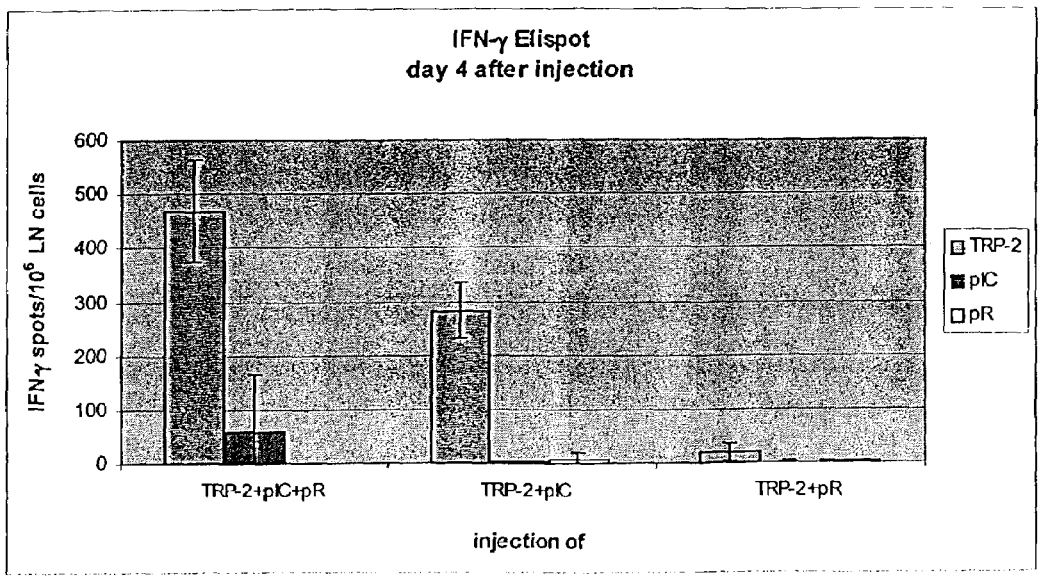
FIG. 4 shows the immune response against a TRP-2-derived peptide after combined injection of pIC and pR; Mice were injected subcutaneously into the footpad with mixtures as indicated. Four days later, draining lymph nodes (LN) were taken and lymph node cells were re-stimulated either with TRP-2-derived peptide, pIC or pR. Number of IFN-γ-producing cells was determined 24 hours later using an ELISPOT assay. Results are shown as the number of spots/1×10$^6$ LN cells±SD of triplicates.

On day 0 mice were injected into each hind footpad with a total volume of 100 μl (50 μl per footpad) containing the above mentioned compounds. Animals were sacrificed 4 days after injection and popliteal lymph nodes were harvested. Preparation of lymph nodes and IFN-γ ELISPOTs were carried out as described in example 1. Results are expressed as the number of spots/1×10$^6$ cells±SD of triplicates. Our results show that pIC and pR also synergistically act in inducing TRP-2 peptide-specific T cells (FIG. 4).

Example 5

The combined application of pIC and pR strongly enhances the induction of T cells specific for a mastocytoma-derived peptide.

| Mice | DBA/2 (Harlan/Olac) |
|---|---|
| Peptide | Mouse mastocytoma P815-derived peptide P1A (LPYLGWLVF), restricted to MHC class I (H2-L$^d$) (Lethe et al., 1992), synthesized by standard solid phase F-moc synthesis, HPLC purified and analysed by mass spectroscopy for purity. Dose: 300 μg/mouse |
| Poly-L-Arginine (pR) | Poly-L-Arginine with an average degree of polymerization of 60 arginine residues; SIGMA Chemicals Dose: 100 μg/mouse |
| Polyinosinic-polycytidylic acid (pIC) | polyinosinic-polycytidylic acid (Sigma Chemicals, P-0913, Lot 125H4024) with the molecular weight ranging from 220,000 to 460,000 Dose: 100 μg/mouse |

Figure 5:
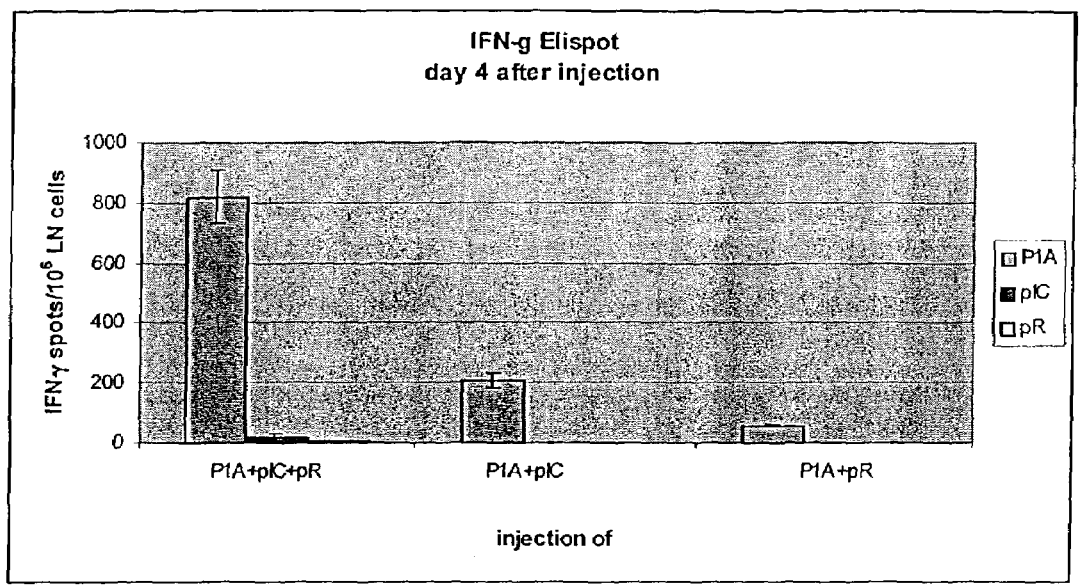
FIG. 5 shows the induction of T cells specific for a P1A (mastocytoma-derived) peptide after combined application of pIC and pR; Mice were injected subcutaneously into the footpad with mixtures as indicated. Four days later, draining lymph nodes (LN) were taken and lymph node cells were re-stimulated either with P1A peptide, pIC or pR. Number of IFN-γ-producing cells was determined 24 hours later using an ELISPOT assay. Results are shown as the number of spots/1×10$^6$ LN cells±SD of triplicates.

Experimental Groups (4 Mice Per Group)
1. P1A-peptide+pIC+pR
2. P1A-peptide+pIC
3. P1A-peptide+pR On day 0 mice were injected into each hind footpad. with a total volume of 100 μl (50 μl per footpad) containing the above mentioned compounds. Animals were sacrificed 4 days after injection and popliteal lymph nodes were harvested. Preparation of lymph nodes and IFN-γ ELISPOTs were carried out as described in example 1. Results are expressed as the number of spots/1×10$^6$ cells±SD of triplicates. As shown in FIG. 5, the combined application of pIC and pR induces strong antigen-specific response also in another mouse strain.

Example 6

The combined application of oligo-dIC$_{26}$ and pR synergistically enhances the immune response against ovalbumin-derived peptide.

| Mice | C57B1/6 (Harlan/Olac) |
|---|---|
| Peptide | OVA$_{257-264}$-Peptide (SIINFEKL), an MHC class I (H-2K$^b$)-restricted epitope of chicken ovalbumin (Rotzschke et al., 1991), was synthesized using standard solid phase F-moc synthesis, HPLC purified and analyzed by mass spectroscopy for purity. Dose: 300 μg/mouse |
| Poly-L-Arginine (pR) | Poly-L-Arginine with an average degree of polymerization of 60 arginine residues; SIGMA Chemicals Dose: 100 μg/mouse |
| Oligo-deoxy IC, 26-mer (oligo-dIC$_{26}$) | oligo-dIC was synthesized by standard phosphoamidid chemistry on a 4 μmol scale and purified by HPLC (NAPS Göttingen, Germany) Dose: 5 nmol/mouse |

Figure 6:
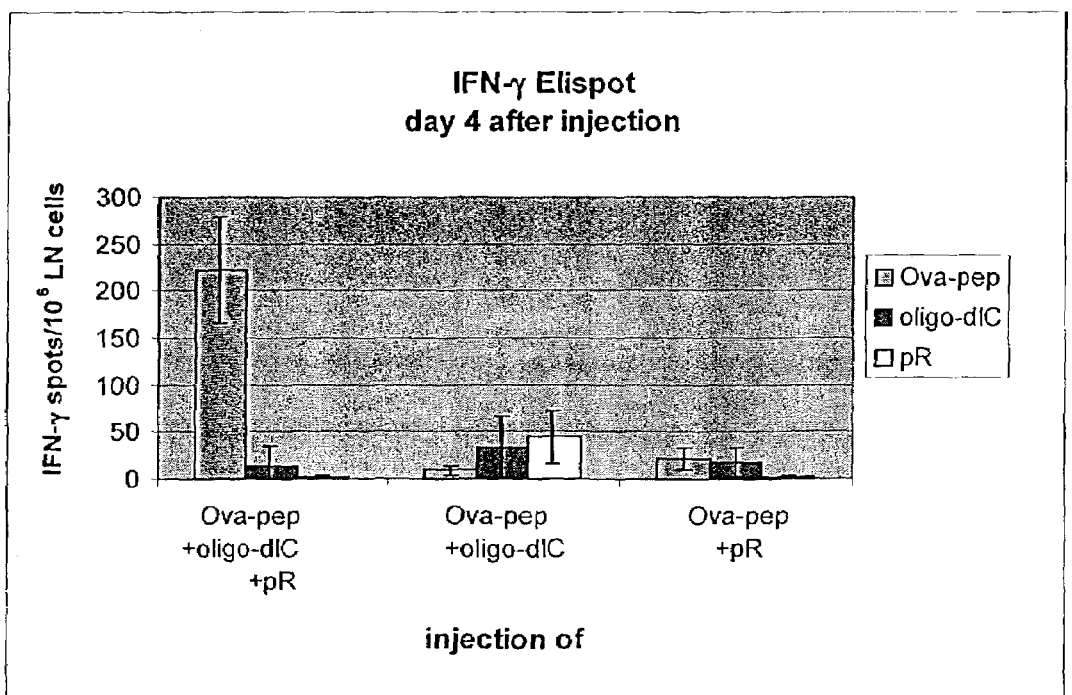
FIG. 6 shows the induction of T cells specific for Ova-derived peptide after combined application of oligo-dIC$_{26}$ and pR; Mice were injected subcutaneously into the footpad with mixtures as indicated. Four days later, draining lymph nodes (LN) were taken and lymph node cells were re-stimulated either with Ova-derived peptide, oligo-dIC$_{26}$ or pR. Number of IFN-γ-producing cells was determined 24 hours later using an ELISPOT assay. Results are shown as the number of spots/1×10$^6$ LN cells±SD of triplicates.

Experimental Groups (4 Mice Per Group)
1. OVA$_{257-264}$-peptide+oligo-dIC$_{26}$+pR
2. OVA$_{257-264}$-peptide+oligo-dIC$_{26}$
3. OVA$_{257-264}$-peptide+pR On day 0 mice were injected into each hind footpad with a total volume of 100 μl (50 μl per footpad) containing the above mentioned compounds. Animals were sacrificed 4 days after injection and popliteal lymph nodes were harvested. Preparation of lymph nodes and IFN-γ ELISPOTs were carried out as described in example 1. Results are expressed as the number of spots/1×10$^6$ cells±SD of triplicates. As shown in FIG. 6, the combined application of oligo-dIC$_{26}$ and pR induces strong peptide-specific T cell response.

Example 7

The antigen-specific immune response against ovalbumin-derived peptide induced by combined injection of poly-L-arginine (pR) and polyinosinic-polycytidylic acid (pIC) is systemic.

| Mice | C57B1/6 (Harlan/Olac) |
|---|---|
| Peptide | OVA$_{257-264}$-peptide (SIINFEKL), an MHC class I (H-2K$^b$)-restricted epitope of chicken ovalbumin (Rotzschke et al., 1991), was synthesized using standard solid phase F-moc synthesis, |

-continued

| | |
|---|---|
| | HPLC purified and analyzed by mass spectroscopy for purity.<br>Dose: 300 μg/mouse |
| Poly-L-arginine (pR) | Poly-L-arginine with an average degree of polymerization of 60 arginine residues; SIGMA Chemicals, P-4663, Lot 68H5903; with the average molecular weight (MW) 10,000<br>Dose: 100 μg/mouse |
| Polyinosinic-polycytidylic acid (pIC) | polyinosinic-polycytidylic acid (Sigma Chemicals, P-0913, Lot 109H4037) with the molecular weight between 220,000 to 460,000 (average length: 500 bp)<br>Dose: 100 μg/mouse |

Experimental Groups (8 Mice Per Group)
1. $OVA_{257-264}$-peptide+pIC+pR
2. $OVA_{257-264}$-peptide+pIC
3. $OVA_{257-264}$-peptide+pR On day 0, mice were injected either into hind footpads or into the flank with a total volume of 100 μl (50 μl per each footpad, 100 μl per flank) containing the above listed compounds. Four mice per group were sacrificed 4 days after injection and draining lymph nodes (popliteal and inguinal lymph nodes for footpad and flank injection, respectively) were harvested. Preparation of lymph nodes and IFN-γ ELISPOTs were carried out as described in example 1.

Figure 7:
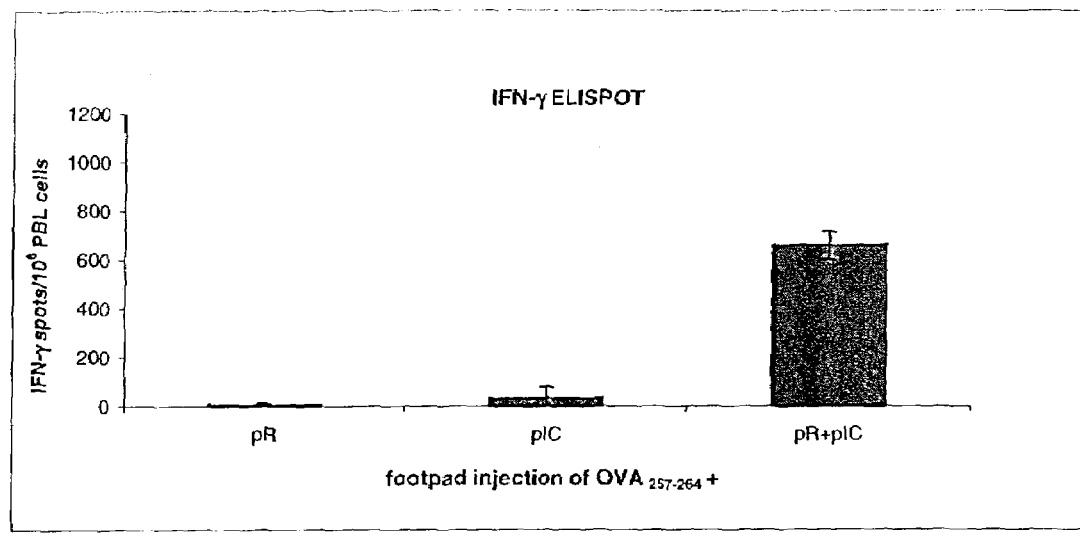
FIG. 7 shows that the combined injection of OVA-derived peptide with pR and pIC induces systemic antigen-specific T cell response; mice were injected subcutaneously either into hind footpads (A) or into the flank (B) with mixtures as indicated. On day 7 after injection, IFN-γ-ELISPOT was carried out with peripheral blood leukocytes (PBLs), which were re-stimulated with OVA$_{257-264}$ peptide. The number of IFN-γ-producing cells was determined 24 hours later. Results are shown as the number of spots/1×10$^6$ PBLs ±SD of duplicates.
Figure 7:
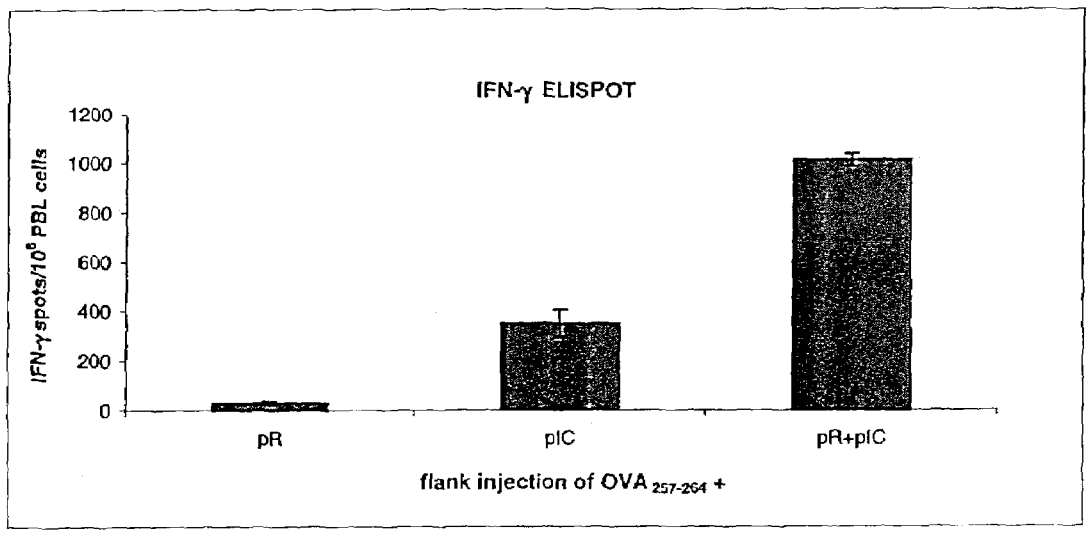

As already shown in previous examples, by injecting OVA-derived peptide in combination with pIC and pR, strong peptide-specific T cell response could be induced on day 4 in draining lymph nodes. To investigate whether the immune response induced by one single injection of peptide with pIC/pR is systemic, the rest of the animals (four per group) was bled from the tail vein at selected time points after injection, peripheral blood leukocytes (PBLs) were isolated, re-stimulated either with the relevant peptide, pIC, pR, ConA (positive control) or medium alone (background) and the number of IFN-γ-secreting T lymphocytes was determined using an ELISPOT assay. Assays were carried out in duplicates. Each spot represents a single IFN-γ-producing T cell. Spots were counted using a Biosys reader (Biosys, Germany). Number of background spots was subtracted from all samples. Results are expressed as the number of spots/$1\times10^6$ cells±SD of duplicates. After the stimulation of PBLs with ConA, many spots demonstrating a good condition of the used lymphocytes could be detected. These results showed that injection of peptide with pIC/pR indeed results in the systemic response as observed on day 7 in peripheral blood (FIGS. 7A, B). In contrast, there was almost no or very weak peptide-specific immune response detectable on day 7 when mice were injected with peptide and pR or peptide and pIC. The strong systemic response induced by single injection of peptide with combination of pR/pIC declined rapidly within the next 30 days.

To determine whether any component of the vaccine could have undesired effects for the host, e.g., induce the systemic release of pro-inflammatory cytokines, animals were injected into hind footpads with combinations as mentioned before, sera from mice were collected one hour after injection and were screened for TNF-α and IL-6 by ELISA. Neither TNF-α nor IL-6 could be detected in the serum of any of the mice, whether injected with peptide/pR, peptide/pIC or peptide and the combination of both substances.

These results indicate that the response induced by injection of peptide antigen with a mixture composed of pIC and pR is systemic.

Example 8

The combined injection of polyinosinic-polycytidylic acid (pIC) and various polycationic compounds synergistically enhances the immune response against ovalbumin-derived peptide.

| | |
|---|---|
| Mice | C57B1/6 (Harlan/Olac) |
| Peptide | $OVA_{257-264}$-peptide (SIINFEKL), an MHC class I (H-2K$^b$)-restricted epitope of chicken ovalbumin (Rotzschke et al., 1991), was synthesized using standard solid phase F-moc synthesis, HPLC purified and analyzed by mass spectroscopy for purity.<br>Dose: 300 μg/mouse |
| Poly-L-arginine (pR) | Poly-L-arginine with an average degree of polymerization of 60 arginine residues; SIGMA Chemicals, P-4663, Lot 68H5903; with the average molecular weight (MW) 10,000<br>Dose: 100 μg/mouse |
| Poly-L-lysine (pL) | Poly-L-lysine, SIGMA Chemicals, P-6516, Lot 78H5910; with the average MW 9,500<br>Dose: 100 μg/mouse |
| Poly-L-ornithine (pO) | Poly-L-ornithine, SIGMA Chemicals, P-4538, Lot 57H5515; with the average MW 10,000<br>Dose: 100 μg/mouse |
| Diethylaminoethyl-dextran (DEAE-dextran) | DEAE-dextran, chloride form, prepared from dextran of the average molecular weight 500,000; SIGMA Chemicals, D-9885, Lot 39H1323<br>Dose: 100 μg/mouse |
| Polyinosinic-polycytidylic acid (pIC) | Polyinosinic-polycytidylic acid (Amersham Pharmacia Biotech, 27-4732, Lot 6034732012)<br>Dose: 50 μg/mouse |

Figure 8:
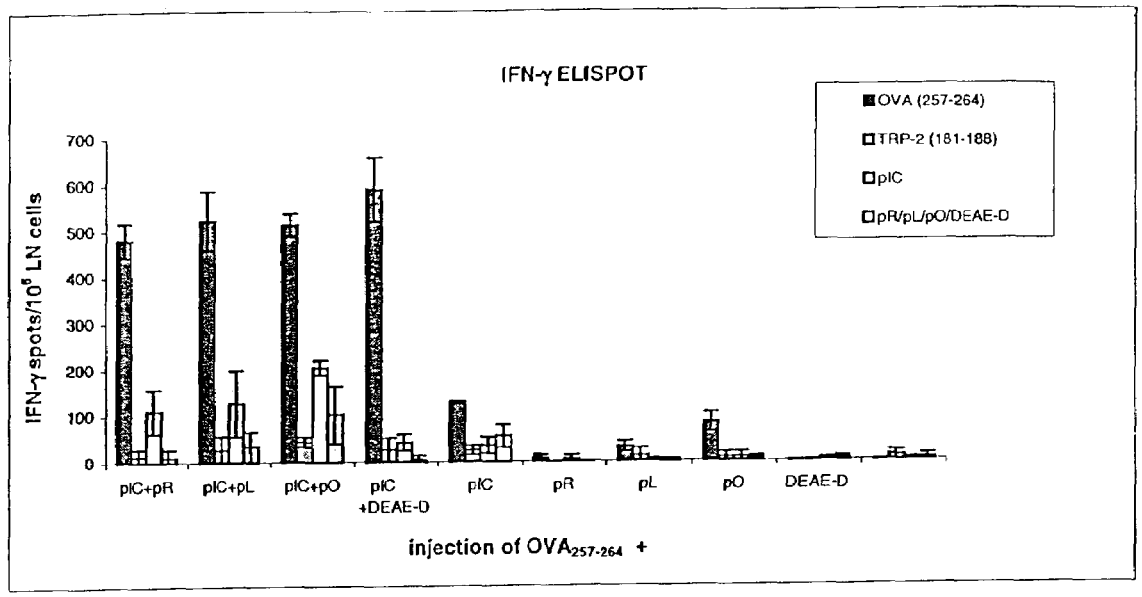
FIG. 8 shows that the combined application of OVA-derived peptide with pIC and various polycationic compounds strongly enhances the induction of peptide-specific T cells. Mice were injected subcutaneously into the footpad with mixtures as indicated. Four days later, draining lymph nodes (LN) were taken and lymph node cells were re-stimulated either with the relevant peptide (OVA$_{257-264}$ peptide), irrelevant peptide (TRP-2$_{181-188}$ peptide), pIC, or the respective polycationic compound. Number of IFN-γ-producing cells was determined 24 hours later using an ELISPOT assay. Results are shown as the number of spots/1×10$^6$ LN cells±SD of triplicates.

Experimental Groups (4 Mice Per Group)
1. $OVA_{257-264}$-peptide+pIC+pR
2. $OVA_{257-264}$-peptide+pIC
3. $OVA_{257-264}$-peptide+pR
4. $OVA_{257-264}$-peptide
5. $OVA_{257-264}$-peptide+pIC+pL
6. $OVA_{257-264}$-peptide+pL
7. $OVA_{257-264}$-peptide+pIC+pO
8. $OVA_{257-264}$-peptide+pO
9. $OVA_{257-264}$-peptide+pIC+DEAE-dextran
10. $OVA_{257-264}$-peptide+DEAE-dextran On day 0, mice were injected into each hind footpad with a total volume of 100 μl (50 μl per footpad) containing the above listed compounds. Animals were sacrificed 4 days after injection and popliteal lymph nodes were harvested. Lymph node cell suspensions were prepared and IFN-γ ELISPOTs were performed as described in Example 1. Results are expressed as the number of spots/$1\times10^6$ cells±SD of triplicates. As shown in FIG. 8, injection of peptide in combination with pIC and any of the above listed polycationic compounds (pR, pL, pO, DEAE-dextran) leads to the strong peptide-specific response. In contrast, injection of peptide with either of the substances alone did not induce peptide-specific T cells. Interestingly, a 50-fold higher amount of DEAE-dextran has to be used in combination with pIC to induce the same numbers of peptide-specific IFN-γ-producing T cells as injection of pIC with any of other used polycationic compounds (pR, pL, pO).

Example 9

The combined injection of ovalbumin (OVA) with poly-L-arginine (pR) and polyinosinic-polycytidylic acid (pIC) synergistically enhances the OVA-specific immune response.

| | |
|---|---|
| Mice | C57B1/6 (Harlan/Olac) |
| Ovalbumin (OVA) | Ovalbumin from chicken egg, grade V, SIGMA Chemicals, A-5503, Lot 54H7070 Dose: 50 μg/mouse |
| Peptides | $OVA_{257-264}$-peptide (SIINFEKL), an MHC class I ($H-2K^b$)-restricted dominant epitope of chicken ovalbumin (Rotzschke et al., 1991), $OVA_{265-280}$-peptide (TEWTSSNVMEERKIKV), an MHC class II ($H-2A^b$)-restricted epitope of chicken ovalbumin (Rotzschke et al., 1991) were synthesized using standard solid phase F-moc synthesis, HPLC purified and analyzed by mass spectroscopy for purity. Dose used for the re-stimulation of lymph node cells: 10 μg/ml. |
| Poly-L-arginine (pR) | Poly-L-arginine with an average degree of polymerization of 60 arginine residues; SIGMA Chemicals, P-4663, Lot 68H5903 Dose: 100 μg/mouse |
| Polyinosinic-polycytidylic acid (pIC) | Polyinosinic-polycytidylic acid (Amersham Pharmacia Biotech, 27-4732, Lot 6034732012) Dose: 50 μg/mouse |

Figure 9:
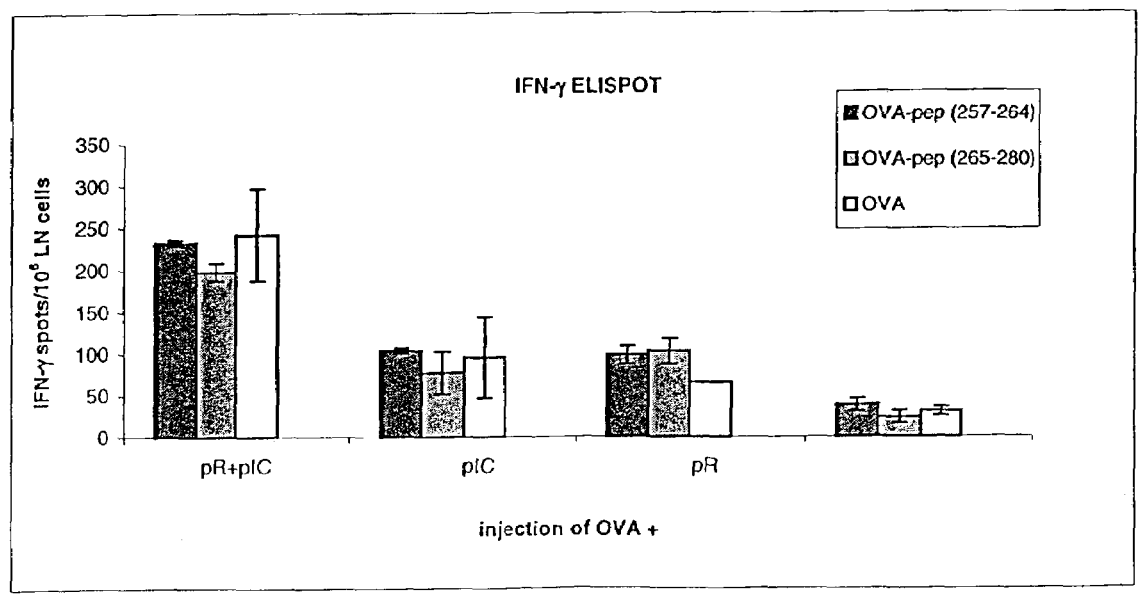
FIG. 9 shows that the combined application of ovalbumin (OVA) with pIC and pR strongly enhances the induction of OVA-specific T cells. Mice were injected subcutaneously into the footpad with mixtures as indicated. Four days later, draining lymph nodes (LN) were taken and lymph node cells were re-stimulated either with MHC class I- and II-restricted OVA-peptides or OVA. The number of IFN-γ-producing cells was determined 24 hours later using an EL-ISPOT assay. The results are shown as the number of spots/1×10$^6$ LN cells±SD of triplicates.

Experimental Groups (4 Mice Per Group)
1. OVA+pIC+pR
2. OVA+pIC
3. OVA+pR
4. OVA On day 0, mice were injected into each hind footpad with a total volume of 100 μl (50 μl per footpad) containing the above listed compounds. Animals were sacrificed 4 days after injection and popliteal lymph nodes were harvested. Lymph node cell suspensions were prepared and IFN-γ ELISPOTs were performed as described in Example 1. Results are expressed as the number of spots/$1\times10^6$ cells±SD of triplicates. As shown in FIG. 9, injection of ovalbumin (OVA) with either pIC or pR leads to the antigen-specific immune response when compared with injection of OVA alone. However, when OVA is injected with a mixture of pIC and pR, the synergizing effect of both substances can be observed, resulting in enhanced antigen-specific T cell response. Importantly, the IFN-γ production was detected not only upon the re-stimulation with the whole OVA protein but also with both, MHC class I ($OVA_{257-264}$)- and II ($OVA_{265-280}$)-restricted OVA-derived epitopes (FIG. 9). These data demonstrate that using the combination of pIC and pR, not only peptides but also whole proteins can be used as an antigen for the vaccine composition.

Example 10

Poly-L-arginine does not affect polyinosinic-polycytidylic acid (pIC)-induced in vitro maturation of DCs.

| | |
|---|---|
| Lipopolysaccharide (LPS) | Lipopolysaccharide from *Escherichia coli*; serotype 055:B5 (SIGMA Chemicals) Dose: 1 μg/ml |
| Poly-L-arginine (pR) | Poly-L-arginine with an average degree of polymerization of 60 arginine residues; SIGMA Chemicals, P-4663, Lot 68H5903 Dose: 10 μg/ml |
| Polyinosinic-polycytidylic acid (pIC) | Polyinosinic-polycytidylic acid (Amersham Pharmacia Biotech, 27-4732, Lot 6034732012) Dose: 10 μg/ml |

Experimental Groups
1. medium
2. LPS
3. pR
4. pIC
5. pR+pIC

It has previously been described that pIC, similar to influenza virus infection, triggers maturation of human DCs in vitro (Cella et al, 1999; Verdijk et al., 1999). Human monocyte-derived DCs were used to investigate how poly-L-arginine affects this pIC-induced DC maturation. Human DCs were generated from monocytes. Briefly, peripheral blood leukocytes (PBLs) were isolated from buffy coats of healthy volunteers by Ficoll gradient centrifugation. Monocytes were isolated from PBLs using CD14-coated magnetic beads (Miltenyi Biotec Inc., Germany) applied according to the manufacturer's instructions. Using this method, we obtained >95% $CD14^+$ cells as determined by flow cytometry. These $CD14^+$ monocytes were cultured in RPMI 1640 medium supplemented with 10% FCS (PAA Laboratories, Linz, Austria), non-essential aminoacids, L-glutamin, gentamycin, sodium pyruvate, 100 ng/ml human GM-CSF and 500 U/ml human IL-4 in 6-well tissue plates for 6–7 days. To this end, the cultures contained >80% MHC class $II^+$/$CD1a^+$ cells (=DCs).

Figure 10:
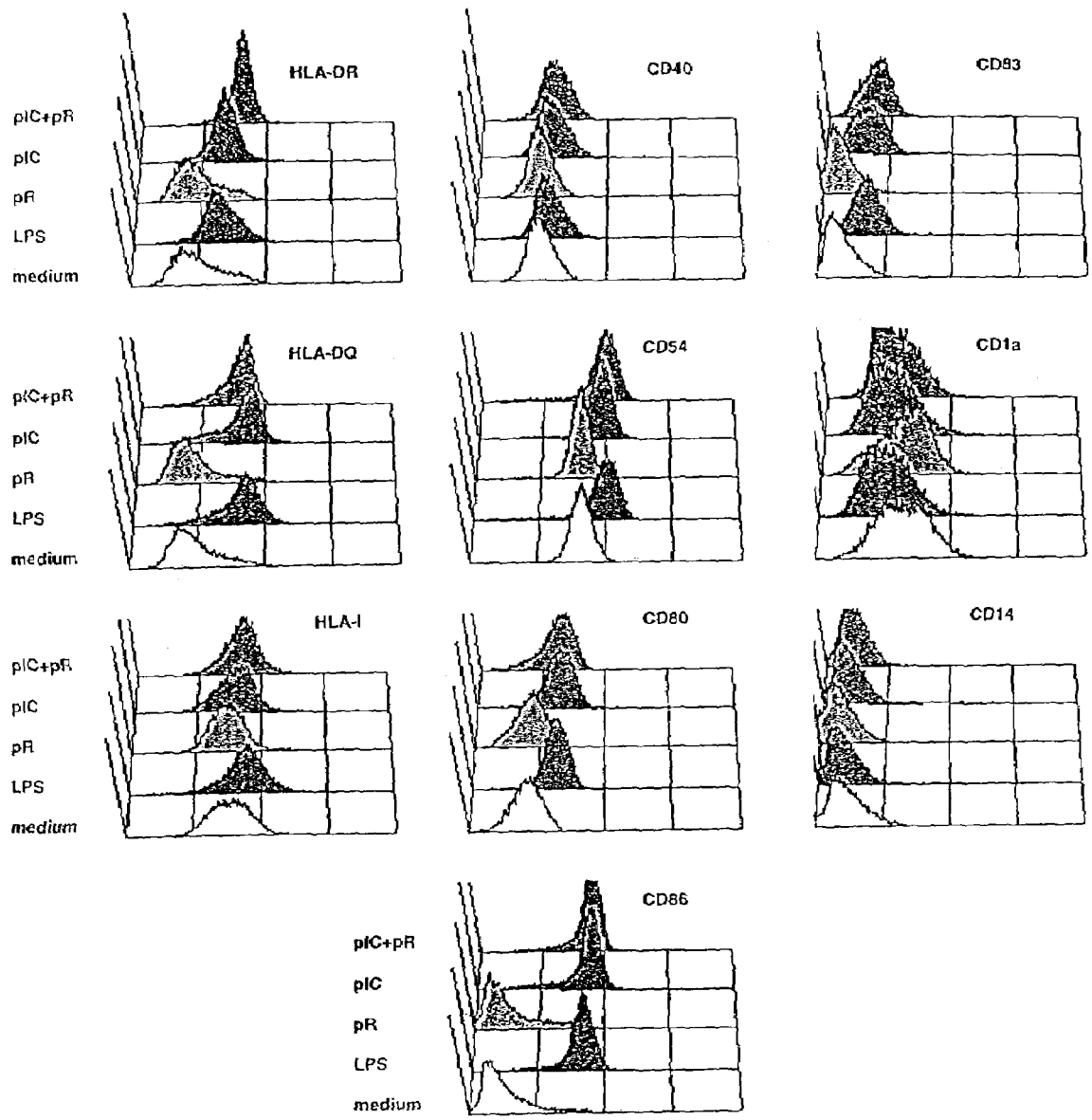
FIG. 10 shows that Poly-L-arginine (pR) does not affect polyinosinic-polycytidylic acid (pIC)-induced in vitro maturation of human DCs. To determine phenotypic maturation, either pIC, pR, both pIC and pR or, for control purposes, LPS and medium alone was added to day 6-cultured human DCs. Extensive phenotypic analysis of surface antigens was performed after 48 hours of stimulation.

To determine phenotypic maturation, day 6-cultured DCs were stimulated either with pIC, pR or with a combination of both substances for 48 hours and were analyzed for the expression of several surface molecules by flow cytometry. For control purposes, DCs were also stimulated with LPS or were left untreated. As shown in FIG. 10, pIC induced an up-regulation of HLA-DR, -DQ and HLA-I molecules, co-stimulatory molecules such as CD40, CD54, CD80, de-novo expression of CD86 and the maturation marker CD83 as well as a down-regulation of CD1a molecules when compared to untreated DCs. The maturation effect of pIC was in all cases comparable to that induced by LPS. In addition, this analysis revealed a slight up-regulation of CD11a, CD11c, CD13, CD25, CD29 and CD50 antigens on DCs upon pIC stimulation. None of the above described phenotypic changes could be observed when DCs were incubated with pR alone. The phenotype of DCs stimulated with a mixture of pIC and pR was similar to that induced by pIC alone (FIG. 10).

Therefore, pIC has the capacity to induce maturation of human DCs in vitro, and pR does not affect this pIC-induced differentiation process.

Example 11

The antigen-specific immune response induced by the combined application of antigen with oligo-deoxyI$C_{26-mer}$ and poly-L-arginine (pR) is systemic.

| | |
|---|---|
| Mice | C57B1/6 (Harlan/Olac) |
| Peptide | OVA$_{257-264}$-peptide (SIINFEKL), an MHC class I (H-2K$^b$)-restricted epitope of chicken ovalbumin (Rotzschke et al., 1991), was synthesized using standard solid phase F-moc synthesis, HPLC purified and analyzed by mass spectroscopy for purity. Dose: 300 µg/mouse |
| Poly-L-arginine (pR) | Poly-L-arginine with an average degree of polymerization of 60 arginine residues; SIGMA Chemicals Dose: 100 µg/mouse |
| Oligo-deoxy IC, 26-mer (oligo-dIC$_{26\text{-}mer}$) | oligo-dIC$_{26\text{-}mer}$ was synthesized by standard phosphoamidid chemistry on a 4 µmol scale and purified by HPLC (NAPS Göttingen, Germany) Dose: 5 nmol/mouse |

Experimental Groups (8 Mice Per Group)
1. OVA$_{257-264}$-peptide+oligo-dIC$_{26\text{-}mer}$+pR
2. OVA$_{257-264}$-peptide+oligo-dIC$_{26\text{-}mer}$
3. OVA$_{257-264}$-peptide+pR
4. OVA$_{257-264}$-peptide On day 0, mice were injected into each hind footpad with a total volume of 100 µl (50 µl per footpad) containing the above listed compounds. Animals (4 mice/group) were sacrificed 4 days after injection and popliteal lymph nodes were harvested. Lymph node cell suspensions were prepared and IFN-γ ELISPOTs were performed as described in Example 1.

Figure 11:
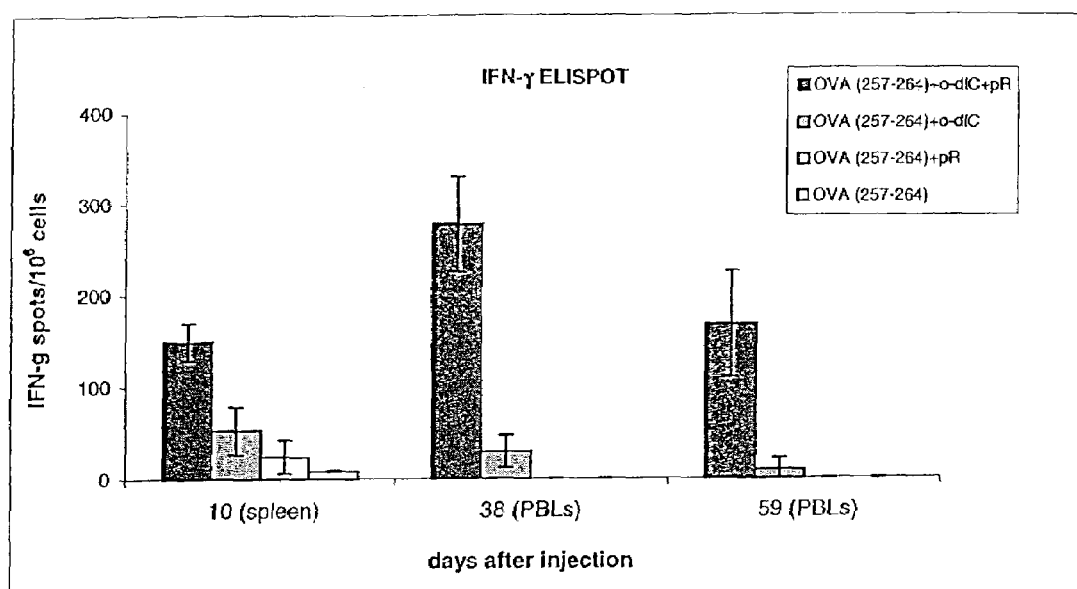
FIG. 11 shows that the combined application of OVA-derived peptide with oligo-dIC$_{26-mer}$ and pR results in the systemic, antigen-specific T cell response. Mice were injected subcutaneously into the footpad with mixtures as indicated in the Figure legend. At selected time points after injection, spleen cells (SCs) or peripheral blood leukocytes (PBLs) were isolated and re-stimulated with OVA-derived peptide. The number of IFN-γ-producing cells was determined 24 hours later using an ELISPOT assay. The results are shown as the number of spots/1×10$^6$ cells±SD of duplicates.

As already shown previously, the combined application of peptide with oligo-dIC$_{26\text{-}mer}$ and pR induced strong antigen-specific response against OVA-derived peptide on day 4 in draining lymph node cells. To examine whether the immune response induced by one single injection of peptide with oligo-dIC/pR is systemic, the rest of the mice (4 mice/group) was investigated at selected time points after injection for the presence of peptide-specific IFN-γ-producing T cells in spleen or peripheral blood using an IFN-γ ELISPOT assay. Results are expressed as the number of spots/1×10$^6$ cells±SD of duplicates. FIG. 11 shows that the response induced by the injection of OVA-derived peptide with oligo-dIC/pR is systemic and lasts at least until day 59 after one single injection (the latest time point of investigation). In contrast, the local or systemic response could not be observed when peptide was injected alone, with oligo-dIC$_{26\text{-}mer}$ or pR.

To determine whether any component of the vaccine could have undesired effects for the host, e.g., induce the systemic release of pro-inflammatory cytokines, animals were injected into hind footpads with combinations as mentioned before, sera from mice were collected one hour after injection and were screened for TNF-α and IL-6 by ELISA. Neither TNF-α nor IL-6 could be detected in the serum of any of the mice, whether injected with peptide/pR, peptide/oligo-dIC or peptide and the combination of both substances.

These results indicate that the response induced by injection of peptide antigen with a mixture composed of oligo-dIC and pR is systemic.

Example 12

The combined application of oligo-deoxyIC$_{26\text{-}mer}$ and poly-L-arginine (pR) enhances the ovalbumin (OVA)-specific T cell response.

| | |
|---|---|
| Mice | C57B1/6 (Harlan/Olac) |
| Ovalbumin (OVA) | Ovalbumin from chicken egg, grade V. SIGMA Chemicals, A-5503, Lot 54H7070 Dose: 50 µg/mouse |
| Peptides | OVA$_{257-264}$-peptide (SIINFEKL), an MHC class I (H-2K$^b$)-restricted dominant epitope of chicken ovalbumin (Rotzschke et al., 1991), OVA$_{265-280}$-peptide (TEWTSSNVMEERKIKV), an MHC class II (H-2A$^b$)-restricted epitope of chicken ovalbumin (Rotzschke et al., 1991) were synthesized using standard solid phase F-moc synthesis, HPLC purified and analyzed by mass spectroscopy for purity. Dose used for the re-stimulation of cells: 10 µg/ml |
| Poly-L-arginine (pR) | Poly-L-arginine with an average degree of polymerization of 60 arginine residues; SIGMA Chemicals, P-4663, Lot 68H5903 Dose: 100 µg/mouse |
| Oligo-deoxy IC, 26-mer (oligo-dIC$_{26\text{-}mer}$) | oligo-dIC$_{26\text{-}mer}$ was synthesized by standard phosphoamidide chemistry on a 4 µmol scale and purified by HPLC (NAPS Göttingen, Germany) Dose: 5 nmol/mouse |

Figure 12:
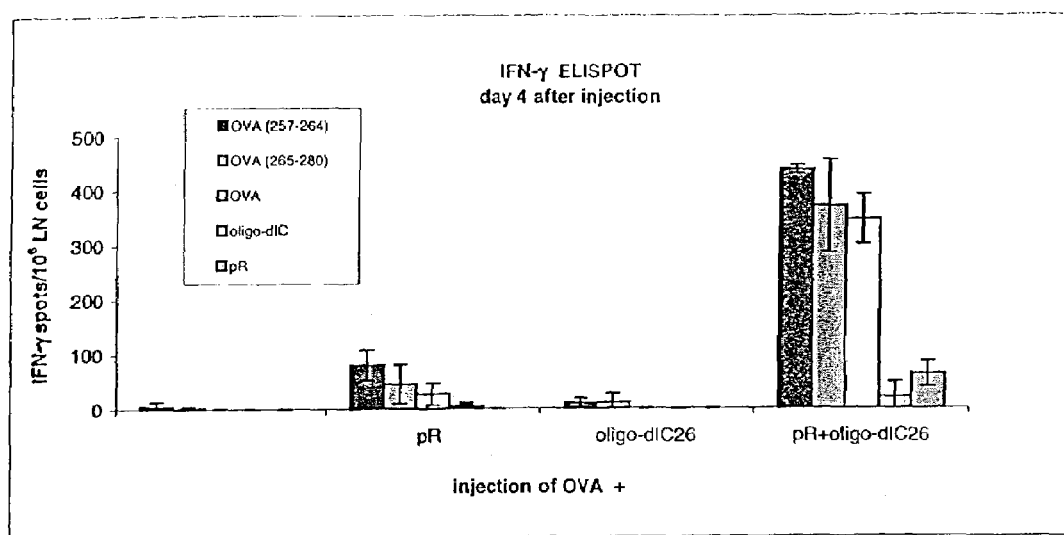
FIG. 12 shows that the combined application of ovalbumin (OVA) with oligo-dIC$_{26-mer}$ and pR strongly enhances the induction of OVA-specific T cells. A) Mice were injected subcutaneously into the footpad with mixtures as indicated. Four days later, draining lymph nodes (LN) were taken and lymph node cells were re-stimulated either with MHC class I- and II-restricted OVA-derived epitopes or OVA. The number of IFN-γ-producing cells was determined 24 hours later using an ELISPOT assay. The results are shown as the number of spots/1×10$^6$ LN cells±SD of triplicates. B) At selected time points after injection, peripheral blood leukocytes (PBLs) were isolated and re-stimulated with OVA$_{257-264}$-peptide. Number of IFN-γ-producing cells was determined 24 hours later using an ELISPOT assay. Results are shown as the number of spots/1×10$^6$ PBLs ±SD of duplicates.
Figure 12:
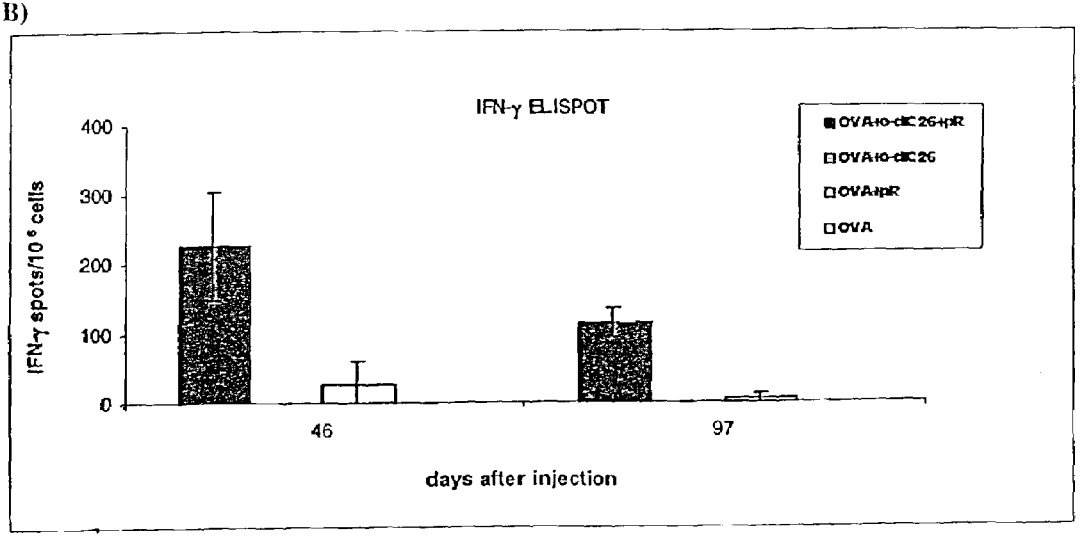

Experimental Groups (8 Mice Per Group)
1. OVA+oligo-dIC$_{26\text{-}mer}$+pR
2. OVA+oligo-dIC$_{26\text{-}mer}$
3. OVA+pR
4. OVA On day 0, mice were injected into each hind footpad with a total volume of 100 µl (50 µl per footpad) containing the above listed compounds. Animals were sacrificed 4 days after injection and popliteal lymph nodes were harvested. Lymph node cell suspensions were prepared and IFN-γ ELISPOTs were performed as described in Example 1. Results are expressed as the number of spots/1×10$^6$ cells±SD of triplicates. As shown in FIG. 12A, injection of ovalbumin (OVA) with a mixture of oligo-dIC and pR results in enhanced antigen-specific T cell response.

Importantly, the IFN-γ production was detected not only upon the re-stimulation with the whole OVA protein but also with both, MHC class I (OVA$_{257-264}$)- and II (OVA$_{265-280}$)-restricted OVA-derived epitopes (FIG. 12A).

To further examine whether the immune response induced by one single injection of OVA protein with oligo-dIC/pR is systemic, the rest of the mice (4 mice/group) was investigated at selected time points after injection for the presence of peptide-specific IFN-γ-producing T cells in peripheral blood using an IFN-γ ELISPOT assay. Results are expressed as the number of spots/1×10$^6$ cells±SD of duplicates. FIG. 12B shows that the response induced by the injection of OVA with oligo-dIC/pR is systemic and persisting at least until day 97 after injection (the latest time point of investigation). In contrast, the local or systemic response could not be observed when OVA was injected alone, with oligo-dIC$_{26\text{-}mer}$ or pR.

These data demonstrate that using the combination of oligo-dIC and pR, not only peptides but also whole proteins can be used as an antigen for the vaccine composition and that the response induced by injection of protein antigen with a mixture composed of oligo-dIC and pR is systemic and longer-lasting.

Example 13

The combined application of oligo-deoxyIC$_{26\text{-}mer}$ and poly-L-arginine (pR) enhances the ovalbumin (OVA)-specific humoral response.

| | |
|---|---|
| Mice | C57B1/6 (Harlan/Olac) |
| Ovalbumin (OVA) | Ovalbumin from chicken egg, grade V, SIGMA Chemicals, A-5503, Lot 54H7070 Dose: 50 µg/mouse |
| Poly-L-arginine (pR) | Poly-L-arginine with an average degree of polymerization of 60 arginine residues; SIGMA Chemicals, P-4663, Lot 68H5903 Dose: 100 µg/mouse |
| Oligo-deoxy IC, 26-mer (oligo-dIC$_{26\text{-}mer}$) | oligo-dIC$_{26\text{-}mer}$ was synthesized by standard phosphoamidide chemistry on a 4 µmol scale and purified by HPLC (NAPS Göttingen, Germany) Dose: 5 nmol/mouse |

Figure 13:
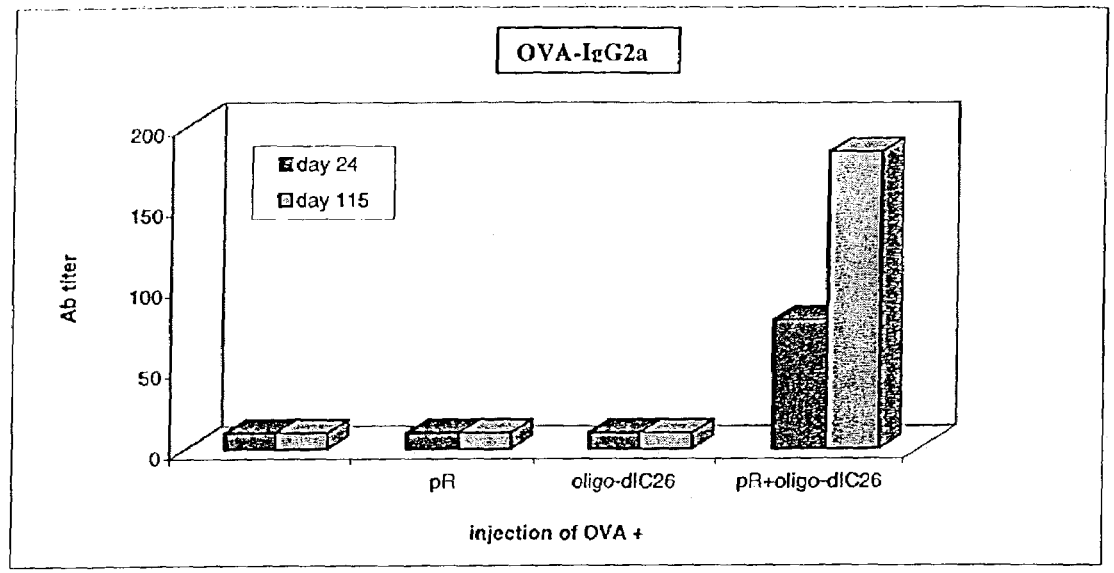
FIG. 13 shows that the combined application of ovalbumin (OVA) with oligo-dIC$_{26-mer}$ and pR enhances production of OVA-specific IgG antibodies. Mice were injected subcutaneously into the footpad with mixtures as indicated. At day 24 and 115 after injection, sera were collected and screened by ELISA for OVA-specific IgG2a (A) and IgG1 (B) antibodies. The results are shown as the antibody titer.
Figure 13:
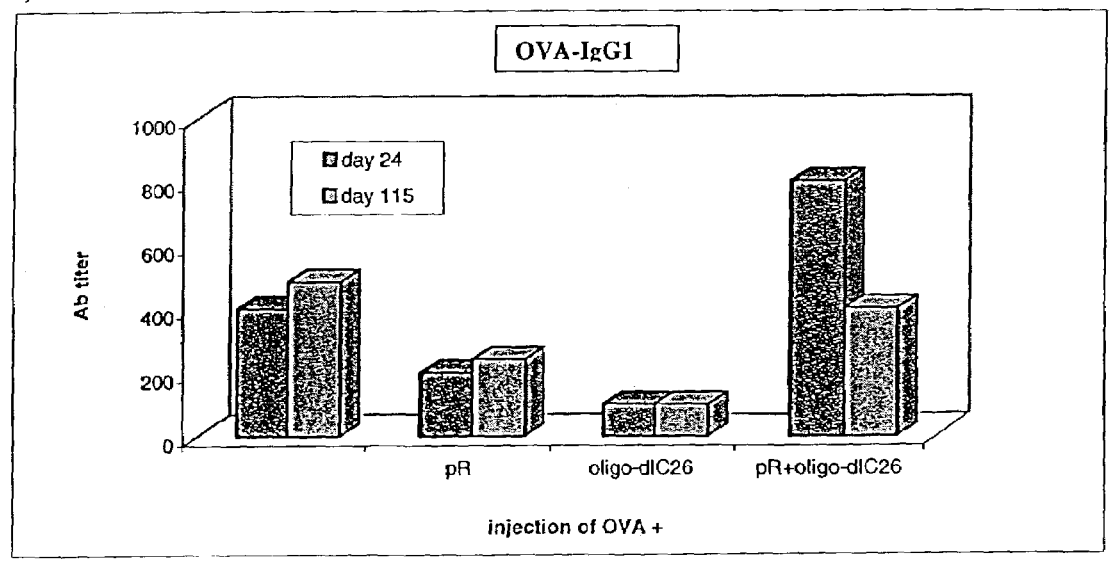

Experimental Groups (4 Mice Per Group)
1. OVA+oligo-dIC$_{26\text{-}mer}$+pR
2. OVA+oligo-dIC$_{26\text{-}mer}$
3. OVA+pR
4. OVA On day 0, mice were injected into each hind footpad with a total volume of 100 µl (50 µl per footpad) containing the above listed compounds. On day 24 after injection, serum was collected and screened by ELISA for the presence of OVA-specific antibodies. These results show that the injection of OVA in combination with oligo-dIC and pR enhanced the production of OVA-specific IgG antibodies when compared with injection of OVA with each of the substances alone (FIG. 13A, B). Interestingly, titers of both IgG2a and IgG1 were increased upon one single injection of OVA with oligo-dIC/pR, implying that both Th1 and Th2 cells were involved. However, after 115 days only the increased IgG2a levels were still detectable in sera of mice injected with OVA and oligo-dIC/pR.

These data demonstrate that the combined injection of OVA with oligo-dIC and pR enhances the OVA-specific humoral response. This response is characterized by the production of both Th1- and Th2-induced antibody isotypes in the early phase, but later, mainly by Th1-induced antibodies.

REFERENCES

Bloom, M. B., Perry-Lalley, D., Robbins, P. F., Li, Y., el-Gamil, M., Rosenberg, S. A., and Yang, J. C. (1997). Identification of tyrosinase-related protein 2 as a tumor rejection antigen for the B16 melanoma. J. Exp. Med. 185, 453–459.

Buschle, M., Schmidt, W., Berger, M., Schaffner, G., Kurzbauer, R., Killisch, I., Tiedemann, J. K., Trska, B., Kirlappos, H., Mechtler, K., Schilcher, F., Gabler, C., and Birnstiel, M. L. (1998). Chemically defined, cell-free cancer vaccines: use of tumor antigen-derived peptides or polyepitope proteins for vaccination. Gene Ther. Mol. Biol. 1, 309–321.

Buschle, M., Schmidt, W., Zauner, W., Mechtler, K., Trska, B., Kirlappos, H., and Birnstiel, M. L. (1997). Transloading of tumor antigen-derived peptides into antigen-presenting cells. Proc. Natl. Acad. Sci. USA 94, 3256–3261.

Cavanaugh, P. F., Jr., Ho, Y-K, and Bardos, T. J. (1996). The activation of murine macrophages and natural killer cells by the partially thiolated double stranded RNA poly (I). mercapto poly (C). Res. Comm. Mol. Pathol. Pharmacol. 91, 131–147.

Cella, M., Salio, M., Sakakibara, Y., Langen, H., Julkunen, I., and Lanzavecchia, A. (1999). Maturation, activation, and protection of dendritic cells induced by double-stranded RNA. J. Exp. Med. 189, 821–829.

Guggenheim, M. A., and Baron, S. (1977). Clinical studies of an interferon inducer, polyriboinosinic-polyribocytidylic acid [Poly (I). Poly (C)], in children. J. Inf. Dis. 136, 50–58.

Hoffmann, J. A., Kafatos, F. C., Janeway, C. A., and Ezekowitz, R. A. (1999). Phylogenetic perspectives in innate immunity. Science 284, 1313–1318.

Lethe, B., van den Eynde, B., van Pel, A., Corradin, G., and Boon, T. (1992). Mouse tumor rejection antigens P815A and P815B: two epitopes carried by a single peptide. Eur. J. Immunol. 22, 2283–2288.

Manetti, R., Annunziato, F., Tomasevic, L., Gianno, V., Parronchi, P., Romagnani, S. and Maggi, E. (1995). Polyinosinic acid polycytidylic acid promotes T helper type 1-specific immune responses by stimulating macrophage production of interferon-a and interleukin-12. Eur. J. Immunol. 25, 2656–2660.

Miyahira, Y., Murata, K., Rodriguez, D., Rodriguez, J. R., Esteban, M., Rodriguez, M. M., Zavala, F. (1995). Quantification of antigen specific CD8$^+$T cells using an ELISPOT assay. J. Immunol. Methods 181, 45–54.

Rammensee, H. G., Friede, T., Stevanovic, S. (1995). MHC ligands and peptide motifs: first listing. Immunogenetics 41, 178–228.

Rotzschke, O., Falk, K., Stevanovic, S., Jung, G., Walden, P., and Rammensee, H. G. (1991). Exact prediction of a natural T cell epitope. Eur. J. Immunol. 21, 2891–2894.

Schmidt, W., Buschle, M., Zauner, W., Kirlappos, H., Mechtler, K., Trska, B., and Birnstiel, M. L. (1997). Cell-free tumor antigen peptide-based cancer vaccines. Proc. Natl. Acad. Sci. USA 94, 3262–3267.

Simmler, M. C., Bruley-Rosset, M, Belpomme, D., and Schwarzenberg, L. (1977). Clinical trial of poly I-poly C as an immunity adjuvant and an immunorestoration agent. Europ. J. Cancer 13, 463–467.

Verdijk, R. B., Mutis, T., Esendam, B., Kamp, J., Melief, C. J. M., Brand, A., and Goulmy, E. (1999). Polyriboinosinic polyribocytidylic acid (poly (I:C)) induces stable maturation of functionally active human dendritic cells. J. Immunol. 163, 57–61.

The invention claimed is:

1. A pharmaceutical composition comprising
   a) an antigen recognized by T-cells and consisting of 6 to 20 amino acid residues, or a mixture of said antigens;
   b) a polycationic peptide; and
   c) a nucleic acid based on inosine and cytosine.

2. The composition of claim 1, wherein the nucleic acid based on inosine and cytosine is poly I: poly C, poly IC, poly dC: poly dI, or poly dIC.

3. The composition of claim 1, wherein the polycationic peptide is polyarginine, polylysine, or a polypeptide containing at least 50% basic amino acid residues.

4. The composition of claim 3, wherein the polycationic peptide is a polypeptide containing least 50% arginine residues, lysine residues, or a combination of arginine and lysine residues.

5. The composition of claim 1, wherein the polycationic peptide contains more than 5 residues.

6. The composition of claim 5, wherein the polycationic peptide contains between 10 and 1000 residues.

7. The composition of claim 6, wherein the polycationic peptide contains between 50 and 500 residues.

8. The composition of claim 1, wherein the antigen is derived from a human, animal or plant pathogen.

9. The composition of claim 1, wherein the antigen is derived from a viral or bacterial pathogen.

10. The composition of claim 1, wherein the antigen is derived from a parasite or plant pathogen.

11. The composition of claim 1, wherein the antigen is further defined as a glycosylated peptide and/or a lipidated peptide.

12. The composition of claim 1, wherein the antigen is further defined as consisting of 7 to 15 amino acid residues.

13. The composition of claim 12, wherein the antigen is further defined as consisting of 8 to 11 amino acid residues.

14. The composition of claim 1, further defined as comprising:
   from 1 ng to 1 g of the antigen;
   from 1 ng to 1 g of the polycationic peptide; and
   from 1 ng to 1 g of the nucleic acid based on inosine and cytosine.

15. The composition of claim 14, further defined as comprising from 1 to 10000 μg of the antigen.

16. The composition of claim 14, further defined as comprising from 0.1 to 1000 µg polycationic peptide.

17. The composition of claim 14, further defined as comprising from 10 µg to 300 mg nucleic acid based on inosine and cytosine.

18. The composition of claim 1, further comprising at least one auxiliary substance or further effective substance.

19. The composition of claim 1, further defined as a vaccine.

20. A method of inducing a systemic immune response comprising:
  a) obtaining a pharmaceutical composition comprising
    i) an antigen recognized by T-cells and consisting of 6 to 20 amino acid residues, or a mixture of said antigens;
    ii) a polycationic peptide; and
    iii) a nucleic acid based on inosine and cytosine;
  b) administering the pharmaceutical composition to a patient.

21. A kit for vaccination comprising:
  a) a component containing an antigen recognized by T-cells and consisting of 6 to 20 amino acid residues, or a mixture of said antigens;
  b) a polycationic peptide; and
  c) a nucleic acid based on inosine and cytosine.

22. A method of eliciting an antigen specific T cell response comprising:
  a) obtaining a pharmaceutical composition comprising
    i) a component containing an antigen recognized by T-cells and consisting of 6 to 20 amino acid residues, or a mixture of said antigens;
    ii) a polycationic peptide; and
    iii) a nucleic acid based on inosine and cytosine; and
  b) administering the pharmaceutical composition to a patient.

* * * * *